United States Patent [19]

Houk

[11] Patent Number: 4,918,022

[45] Date of Patent: Apr. 17, 1990

[54] ANALYSIS OF BULK ASBESTOS SAMPLES

[75] Inventor: Clifford C. Houk, Athens, Ohio

[73] Assignee: Ohio State University, Athens, Ohio

[21] Appl. No.: 323,376

[22] Filed: Mar. 13, 1989

[51] Int. Cl.$^4$ ............................................. G01N 31/22
[52] U.S. Cl. .................................... 436/79; 250/461.1; 422/82.08; 436/164; 436/172
[58] Field of Search ................... 436/72, 172, 164, 79; 250/461.1, 461.2, 459.1; 422/68

[56] References Cited

U.S. PATENT DOCUMENTS

| | | | |
|---|---|---|---|
| 3,881,822 | 5/1975 | Rose | 436/72 |
| 4,333,733 | 6/1982 | Sanford et al. | 436/88 |
| 4,383,043 | 5/1983 | Denney et al. | 436/74 |

OTHER PUBLICATIONS

"Test for Screening Asbestos," Kim, W. S.; Carter, J. W., II; Kupel, R. E.; DHEW (NIOSH), Pub. No. 80-110; Oct. 1979.

Jones, William L., "Identification of Chrysotile," NTIS publication, Feb. 25, 1981, #PB81-222663.

The Merck Index, 10th Edition, pub. Rayway, N.J., 1983, p. 333, #2312–"Clayton Yellow".

Albright et al, Research on a Rapid and Simple Detection Method for Asbestos, R&D Report for National Science Foundation, 1980.

Albright et al, A Fluorescent Dye Building Technique for Detection of Chrysotile Asbestos, Microscope, 1982, pp. 267–280.

Primary Examiner—Christine M. Nucker
Assistant Examiner—Jill Johnston
Attorney, Agent, or Firm—Killworth, Gottman, Hagan & Schaeff

[57] ABSTRACT

A process for determining the presence of the chrysotile form of asbestos in a bulk sample is provided. A small sample of a material suspected to contain asbestos is mixed with a phosphate buffer solution containing Clayton Yellow dye. The sample is then exposed to ultraviolet light. Fluorescence of the sample indicates the presence of chrysotile.

6 Claims, No Drawings

ANALYSIS OF BULK ASBESTOS SAMPLES

BACKGROUND OF THE INVENTION

This invention relates to an analytical chemistry method involving fluorescence, and more particularly to a method for determining the presence of chrysotile in a product sample.

Many manufactured products such as talc, construction materials, paints, and insulation have been known to contain various forms of asbestos, a form of impure magnesium silicate which has been implicated as a possible cause of cancer. Presently the form of asbestos which is the most abundant form found in the United States and which causes physiological concern is chrysotile, a hydrated magnesium silicate which may be represented as $Mg_3Si_2O_5(OH)_4$. Chrysotile has a serpentine structure with an infinite number of crosslinked $(Si_2O_5)^{-2}$ portions and comprises a macroanion.

Because of the health concern, and the number of public and private buildings which have been constructed of materials which may contain chrysotile, a quick and reliable test for the detection of chrysotile is needed. Presently, if a bulk sample of material is found to contain 1% of more asbestos, abatement, disposal, or encapsulation of the material must be undertaken. It would be desirable to have a simple, reliable test which can be done on site to make the determination.

Several procedures have been developed for determining the presence of chrysotile. Two commonly known methods are X-ray diffraction and microscopic examination. However, these methods are not very reliable because X-ray diffraction is uncertain when working with samples containing low percentages of chrysotile, and microscopic examination often fails because the particles approach the limit of resolution of the instrument. Further, neither of these procedures is practical for field testing of bulk samples because of the equipment required and the need for trained technicians to operate that equipment.

Another procedure developed by Rose (U.S. Pat. No. 3,881,822) involves a spectrophotometric method for determining the chrysotile content in talc based on the preferential absorption of sulfonphthalein dyes by chrysotile but not by talc. However, this procedure is limited in that it relates only to determining the concentration of chrysotile in talc.

Other attempts have been made to determine the presence of chrysotile through a a fluorescent dye binding technique. (Albright et al. Microscope, pp. 267–280, (1982); Albright et al. R & D Report for National Science Foundation, Research on a Rapid and Simple Detection Method for Asbestos, 1980). When testing 26 different fluorescent organic dye compounds for binding affinity to chrysotile asbestos, two organic dyestuffs, Morin and 4,5-dihydroxy-naphthalene-2,7-disulfonic acid (DHNDS) were found to bind with chrysotile fibers at or near a pH of 11.4. However, the determination of which dyes will bind with chrysotile appears to be unpredictable.

Accordingly, there is a need to provide a rapid, simple, and accurate method for determining the presence of chrysotile in various product samples.

SUMMARY OF THE INVENTION

This invention provides an improved procedure for determining the presence of chrysotile in various product samples such as building materials, talc, paints, and insulation which avoids the uncertainty involved in using certain prior art procedures. This is accomplished through the use of a fluorescent dye which binds to chrysotile, allowing easy detection of chrysotile in products through the use of ultraviolet light.

A small product sample suspected by containing asbestos is obtained and placed in a reaction vessel along with a pre-measured amount of basic buffered reagent and Clayton Yellow (trademark of Clayton Anilene Co. Ltd.) dye. The reaction vessel is then capped and the sample, reagent, and dye are mixed. Binding of the dye with chrysotile is rapid, and the sample can be analyzed within as little as five minutes after mixing. The sample is then placed under ultraviolet light. Fluorescence of the sample indicates the presence of chrysotile. Because fluorescence occurs in the red region of visible light (approx. 650–750 nm.), no special equipment is required. The color will be visible to the naked eye.

Accordingly, it is an object of the present invention to provide a rapid and accurate method for determining the presence of chrysotile which avoids the uncertainty of prior art procedures and yet provides a simple process for on-site detection.

Other objects and advantages of the invention will be apparent from the following description and the appended claims.

DESCRIPTION OF THE PREFERRED EMBODIMENT

In the process of this invention, a product sample such as a building or construction material, talc, paint, or insulation is tested for the presence of chrysotile by mixing it with a buffered reagent and Clayton Yellow dye in a reaction vessel, whereby the sample tests positive for chrysotile if it fluoresces under ultraviolet light.

A small product sample, preferably weighing from 10–100 mg., is obtained with a sampling tool and placed in a reaction vessel along with a pre-measured amount of phosphate buffer reagent and Clayton Yellow dye. Preferably, approximately 1.0 ml of the buffer and dye solution is used, with the dye concentration in the buffer being $\geq 0.0001\%$ by weight. The order of addition of the reactants and sample to the vessel is not critical, and will not affect the results obtained. It is preferred that the reagent have a pH of 11.4 since the surface charge of chrysotile can be modified by pH (chrysotile has an isoelectric point of pH 11.4). Clayton Yellow (trademark of Clayton Anilene Co. Ltd.) dye, preferably dissolved in alcohol, is used because of its high binding affinity to and specificity for chrysotile. Clayton Yellow dye is the disodium salt of 2,2'-(1-triazine-1,3-diyldi-4,1-phenylene)bis[6-methyl-7-benzothiazolesulfonic acid]. It has a Colour Index No. of 19540, and its chemical formula is as follows:

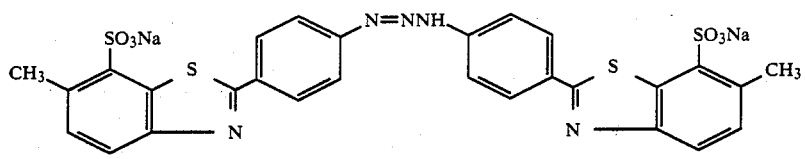

The reaction vessel containing the product sample, reagent, and dye is capped and mixed. The mixture is preferably allowed to stand in the reaction vessel for approximately five minutes after mixing to allow sufficient binding to take place. Finally, the sample is placed under ultraviolet light, preferably having a wavelength of less than 400 nanometers. Fluorescence of the product sample indicates that chrysotile is present.

The process of the present invention can accurately detect the presence of chrysotile in a bulk sample down to approximately 1% concentration (i.e., chrysotile content of the total sample). The process is also believed to be effective in detecting chrysotile concentrations of less than 1%. However, it may be necessary to use equipment such as a photomultiplier to aid in detecting fluorescence at such a low concentration.

In order that the invention may be more readily understood, reference is made to the following example, which is intended to illustrate the invention, but is not to be taken as limiting the scope thereof.

Example

Seventy bulk samples of material were tested using the process of the present invention to detect the presence or absence of chrysotile in the samples. The samples had previously been analyzed using polarized light microscopy techniques to determine the presence or absence of chrysotile. Of these samples which tested positive for the presence of chrysotile, the chrysotile content ranged from <1% to >75% by weight.

All samples were tested using 1.0 ml of a phosphate buffer reagent solution containing a Clayton Yellow dye concentration of between 0.00005 and 0.00015% by weight. The results are reported in Table I below. As can be seen, 100% accuracy was achieved in the identification of the samples.

TABLE I

| No. of Samples | No. Correct | % Accuracy | False Negatives | False Positives |
|---|---|---|---|---|
| 70 | 70 | 100% | 0 | 0 |

Having described the invention in detail and by reference to preferred embodiments thereof, it will be apparent that modifications and variations are possible without departing from the scope of the invention defined in the appended claims.

What is claimed is:

1. A process for detecting the presence of chrysotile in a product sample comprising the steps of:
   (a) selecting a product sample suspected to contain chrysotile;
   (b) mixing said sample along with a predetermined amount of basic buffered reagent solution containing a 2,2'-(1-triazene-1,3-diyldi-4,1-phenylene)-bis[6-methyl-7-benzothiazolesulfonic acid) disodium salt dye concentration of between about 0.00005 and 0.00015% by weight; and
   (c) placing said sample under ultraviolet light whereby fluorescence of said sample indicates the presence of chrysotile.

2. The process of claim 1 wherein said product sample weighs approximately 10–100 mg.

3. The process of claim 1 wherein said buffered reagent used is a phosphate buffer having a pH of 11.4.

4. The process of claim 1 wherein said Clayton Yellow dye is dissolved in alcohol.

5. The process of claim 1 wherein the mixture of reagent and product sample is allowed to stand for approximately 5 minutes.

6. The process of claim 1 wherein the wavelength of said ultraviolet light is less than 400 nanometers.

* * * * *

UNITED STATES PATENT AND TRADEMARK OFFICE
CERTIFICATE OF CORRECTION

PATENT NO. : 4,918,022

DATED : April 17, 1990

INVENTOR(S) : Clifford C. Houk

It is certified that error appears in the above-identified patent and that said Letters Patent is hereby corrected as shown below:

On the title page, [73] Assignee "Ohio State University" should be --Ohio University--.

Signed and Sealed this

Third Day of December, 1991

*Attest:*

HARRY F. MANBECK, JR.

*Attesting Officer*  *Commissioner of Patents and Trademarks*